United States Patent
Pieger

(10) Patent No.: US 7,800,087 B2
(45) Date of Patent: Sep. 21, 2010

(54) WORKROOM PARTITION

(75) Inventor: Markus Pieger, Stuttgart (DE)

(73) Assignee: Trumpf Laser- und Systemtechnik GmbH, Ditzingen (DE)

( * ) Notice: Subject to any disclaimer, the term of this patent is extended or adjusted under 35 U.S.C. 154(b) by 386 days.

(21) Appl. No.: 11/868,118

(22) Filed: Oct. 5, 2007

(65) Prior Publication Data

US 2008/0173830 A1      Jul. 24, 2008

(30) Foreign Application Priority Data

Oct. 5, 2006    (EP)    ................... 06020907

(51) Int. Cl.
G21F 7/00    (2006.01)
A47G 5/00    (2006.01)

(52) U.S. Cl. ................. 250/517.1; 250/205; 250/515.1; 128/846; 128/849; 219/121.6; 219/121.63; 606/2

(58) Field of Classification Search ................. 250/205, 250/515.1, 517; 128/846, 849; 160/135; 219/121.6, 121.63; 606/2

See application file for complete search history.

(56) References Cited

U.S. PATENT DOCUMENTS

| 4,575,610 | A | * | 3/1986 | Gavin ....................... 219/121.6 |
|---|---|---|---|---|
| 4,650,287 | A | * | 3/1987 | Kudo et al. ............... 250/515.1 |
| 4,839,495 | A | * | 6/1989 | Kitera et al. ........... 219/121.63 |
| 4,901,738 | A | * | 2/1990 | Brink et al. ................. 128/849 |
| 5,151,095 | A | * | 9/1992 | Teeple, Jr. ....................... 606/2 |
| 5,212,387 | A | * | 5/1993 | Swan ....................... 250/515.1 |
| 5,309,925 | A | * | 5/1994 | Policastro ................... 128/849 |
| 5,992,417 | A | * | 11/1999 | Toepel ........................ 128/846 |
| 6,107,597 | A | * | 8/2000 | Staschewski et al. ... 219/121.63 |
| 6,518,586 | B1 | * | 2/2003 | Heberer ................... 250/515.1 |
| 6,571,852 | B2 | * | 6/2003 | Toepel ......................... 160/135 |
| 7,432,789 | B2 | * | 10/2008 | Barnklau et al. ............ 335/157 |
| 2005/0103755 | A1 | | 5/2005 | Baker et al. |

FOREIGN PATENT DOCUMENTS

DE    202006006823    8/2006
GB    2 182 746    5/1987

* cited by examiner

*Primary Examiner*—David A Vanore
(74) *Attorney, Agent, or Firm*—Fish & Richardson P.C.

(57) ABSTRACT

A workroom partition divides a workroom interior of a workroom and a workroom surroundings. The workroom is provided with a laser processing device. The workroom partition includes on its inner side facing the laser processing device, a laser beam reflector formed from pre-fabricated reflective sheet of material having a grained reflective surface structure that faces the laser processing device, by means of which the majority of laser radiation incident on the laser beam reflector and originating from the laser processing device is diffusely reflectable.

22 Claims, 7 Drawing Sheets

WORKROOM PARTITION

CROSS REFERENCE TO RELATED APPLICATION

This application claims priority under 35 U.S.C. §119(a) to European Application No. 06 020 907.9, filed on Oct. 5, 2006, the entire contents of which are hereby incorporated by reference.

TECHNICAL FIELD

The invention relates to a workroom partition between an interior of a workroom and the workroom surroundings, where the workroom houses a laser processing device.

BACKGROUND

Workrooms in which laser processing devices are operated are shielded with respect to their surroundings, for example, for reasons of industrial safety. According to the pertinent safety regulations, harmful laser radiation produced by a laser processing device within a workroom should be contained within the workroom and should not be able to escape from an interior of the workroom into the area surrounding the workroom even under irregular operating states of the laser processing device, and at least for a limited period. Workroom partitions, known as "laser screens", can be used for this purpose.

A workroom of the generic kind and a workroom partition of the generic kind are disclosed in U.S. Pat. No. 4,650,287. In the prior art, a workroom that houses a laser processing tool is enclosed by a radiation-absorbing laser screen. The known laser screen is a composite construction including a metal sheet on the outer side of the screen remote from the laser processing tool and a radiation-absorbing coating that is applied to the inner side of the metal sheet situated towards the laser processing tool. The radiation-absorbing coating is formed by metal oxides, for example, by oxides of aluminum, titanium, zirconium, magnesium, and/or chromium. The ability of these metal oxide coatings to absorb laser radiation is described as excellent in U.S. Pat. No. 4,650,287. The laser screen in U.S. Pat. No. 4,650,287 therefore acts as a radiation trap absorbing the majority of the energy of the laser radiation.

SUMMARY

In one general aspect, a workroom partition is between a workroom interior of a workroom and a workroom surroundings. The workroom is provided with a laser processing device. The workroom partition includes on its inner side facing the laser processing device, a laser beam reflector formed from pre-fabricated reflective sheet of material having a grained reflective surface structure that faces the laser processing device, by means of which the majority of laser radiation incident on the laser beam reflector and originating from the laser processing device is diffusely reflectable.

Implementations can include one or more of the following features. For example, the laser beam reflector is matched in terms of its material to the wavelength of the laser radiation to be reflected. The grained reflective surface structure can include a shiny metal surface. The laser beam reflector can be made of an aluminum sheet, a copper sheet, a molybdenum sheet, a chromium sheet, a silver sheet, or a gold sheet having a surface that is diffusely reflective. The laser beam reflector can include at least partially a reinforcing deformation. The laser beam reflector can include a portion that is at least partially in the form of trapezoidal metal sheeting.

The workroom partition can include an outer layer that faces the workroom surroundings and is remote from the laser processing device. The laser beam reflector can be disconnectably connected to the outer layer of the workroom partition. The laser beam reflector can be connected to the outer layer of the workroom partition such that a gap is formed between the laser beam reflector and the outer layer of the workroom partition.

In another general aspect, a workroom includes a laser processing device, and a workroom partition that separates a workroom interior from a workroom surroundings and houses the laser processing device. The workroom partition includes on its inner side facing the laser processing device, a laser beam reflector formed from pre-fabricated reflective sheet of material having a grained reflective surface structure that faces the laser processing device, by means of which the majority of laser radiation incident on the laser beam reflector and originating from the laser processing device is diffusely reflectable.

Implementations can include one or more of the following features. For example, the laser beam reflector can be matched in terms of its material to the wavelength of the laser radiation to be reflected. The grained reflective surface structure can include a shiny metal surface. The laser beam reflector can be made of an aluminum sheet, a copper sheet, a molybdenum sheet, a chromium sheet, a silver sheet, or a gold sheet having a surface that is diffusely reflective. The laser beam reflector can include at least partially a reinforcing deformation. The laser beam reflector can include a portion that is at least partially in the form of trapezoidal metal sheeting.

The workroom partition can include an outer layer that faces the workroom surroundings and is remote from the laser processing device, wherein the laser beam reflector is disconnectably connected to the outer layer of the workroom partition. The laser beam reflector can be connected to the outer layer of the workroom partition such that a gap is formed between the laser beam reflector and the outer layer of the workroom partition.

In another general aspect, a method includes obtaining a pre-fabricated reflective sheet of material having a grained reflective surface structure, forming a workroom partition at least in part from the obtained pre-fabricated reflective sheet such that the grained surface structure faces an interior of a workroom, where the workroom partition separates the workroom interior from the workroom surroundings, housing a workpiece and a laser processing device including a laser in the interior of the workroom such that a laser beam from the laser is at least partly directed to the workpiece for processing of the workpiece, and diffusely reflecting a majority of laser radiation incident on the grained surface structure such that laser radiation is mostly contained within the workroom interior without causing damage to the workroom interior.

Implementations can include one or more of the following features. For example, the method can further include selecting a material of the laser beam reflector depending on a wavelength of the laser beam produced by the laser in the workroom such that the majority of the laser radiation is reflected by the laser beam reflector on the grained surface structure.

The pre-fabricated sheet of material can be a pre-fabricated sheet of aluminum material. The pre-fabricated sheet can be disconnectably connected to an outer layer of the workroom partition, where the outer layer is arranged to face the workroom surroundings and to be remote from the laser processing device. A gap can be formed between the pre-fabricated reflective sheet and an outer layer of the workroom partition, where the outer layer is arranged to face the workroom surroundings and to be remote from the laser processing device. The pre-fabricated reflective sheet can be applied to a ceiling of the workroom partition. The workroom interior can be enclosed by the workroom partition. The workroom partition can be formed of at least four walls and a ceiling to form an enclosed space. The workroom partition can be formed by forming at least one window, at least one door, or both a window and a door into at least one of the four walls to enable an operator to view the workroom interior.

In one general aspect, a laser beam reflector that reflects the majority of the laser radiation to be prevented from leaving the interior of the workroom is provided on the inner side of the workroom partition. The high reflectance of the laser beam reflector prevents radiation energy of the laser radiation incident on the laser beam reflector from being coupled into the workroom partition to an extent that even after a short time would lead to overheating and to an associated destruction of the workroom partition. In this respect, the features of the invention ensure maximum industrial safety.

At the same time, the incident laser radiation is not directionally but rather diffusely reflected by the laser beam reflector. In consequence of its scattering, the reflected laser radiation has merely a low energy density and is therefore not able to do damage in the interior of the workroom, in particular to the laser processing device arranged there. In this respect, the workroom partition ensures that the operational reliability of the laser processing device is maximized or improved. Protective devices to be used otherwise on the laser processing device, for example, protective covers for bellows, can be dispensed with.

The laser processing device can be operated with high-power laser radiation and still maintain industrial safety and operational reliability.

The laser beam reflector can be matched in terms of material to the wavelength of the laser radiation to be reflected. In this way, one can ensure that the majority of the laser radiation incident on the laser beam reflector is indeed actually reflected. The wavelength of the laser light to be reflected is dependent on the construction of the radiation source. For instance, up to 99% of $CO_2$ laser light and up to 90% of NdYAG laser light can be reflected at a laser beam reflector of aluminum. Generally, laser beam reflectors having a reflectance of at least 90% are preferred. At such a reflectance of the laser beam reflector, it is possible to ensure that the service life of the workroom partition will be adequate.

Especially practical are laser beam reflectors in the form of diffusely reflecting metal surfaces. Such laser beam reflectors can be manufactured comparatively simply, and by virtue of their robustness exhibit the required reflectivity even under tough operating conditions and over a long period of use.

Various metals can be considered as materials for metal surfaces acting as laser beam reflectors. For example, a diffusely reflecting aluminum surface is preferred as the laser beam reflector. Such laser beam reflectors are particularly inexpensive. In addition, the use of aluminum as reflector material is advisable owing to its comparatively (compared with copper, for example) low thermal conductivity and owing to its low weight. Finally, at different wavelengths of the laser light to be reflected, a high reflectance can be achieved with aluminum.

For the sake of simplicity, and in the interests of a manufacture that is as simple and as cost-effective as possible, a shiny surface, optionally a shiny metal surface, is preferred as the diffusely reflective surface forming the laser beam reflector.

The laser beam reflector, optionally the metal surface forming the laser beam reflector, can be formed by a coating applied to a substrate. Coating methods that can be considered are, for example, flame spraying or metal deposition methods.

In the interests of a simple and cost-effective manufacture, it is advisable to provide directly a surface of a reflector body as the laser beam reflector. In this case there is no need for a surface coating serving as the laser beam reflector to be applied to a substrate.

In one implementation, a metal body, for example, a metal sheet, is provided as the reflector body forming with its surface the laser beam reflector. An aluminum sheet that forms with a shiny and diffusely reflective aluminum surface the laser beam reflector is preferred.

A diffuse reflection of the incident laser radiation by the laser beam reflector can be effected in accordance with the invention in different ways.

For reasons associated with production, it is advisable to provide the laser beam reflector with an appropriate three-dimensional surface structure. An especially intense scattering of the reflected laser light can be achieved by means of irregularly profiled surface structures. Laser beam reflectors having a regularly profiled surface structure are nevertheless also possible. For example, surface structures can be produced by stamping, for example, on sheet metals that form the laser beam reflector directly with their surface.

Grained surface structures are commercially obtainable (pre-fabricated) and thus advantageously freely available.

An optimum or improved efficiency of laser beam reflectors presupposes the stability of their shape. To ensure this stability of shape, reinforcing deformations can be provided on the substrate provided with a diffusely reflecting coating or on the reflector body forming a diffusely reflecting surface. Trapezoidal metal sheetings are examples of commercially available structures and hence easily obtainable substrates or reflector bodies. Reinforcements of the this kind are advantageous, for example, when the laser beam reflector is provided in the ceiling region of the workroom or the workroom partition.

The laser beam reflector can be part of a workroom partition, which additionally includes an outer layer, which in turn is arranged on the side of the laser beam reflector remote from the laser processing device. The laser beam reflector can be disconnectably connected to the outer layer of the workroom partition. By virtue of this disconnectable connection, it is possible, for example, to exchange a defective or worn laser beam reflector in a simple manner for a fully functioning laser beam reflector. A laser beam reflector can also be removed without difficulty from the associated outer layer of the workroom partition, for instance, in order to carry out maintenance work, especially cleaning work, and after maintenance or cleaning can be mounted on the outer layer again.

In the interests of a thermal insulation of the outer layer of the workroom partition against the laser beam reflector, a gap can be maintained between the laser beam reflector and the outer layer of the workroom partition.

The laser beam partition is not destroyed upon being struck by a stray laser beam so that the laser beam partition can be re-used or used continuously to process workpieces. Additionally, the workpiece manufacturing process does not need to be shut down if the laser beam strays from the workpiece because the laser beam does not destroy the laser beam partition and is reflected in a diffuse manner such that the reflected light has less power per surface area than the laser beam impinging upon the laser beam partition. The workroom is designed to have industrial safety combined with maximum operational reliability of the laser processing device housed in the workroom.

DETAILED DESCRIPTION

Figure 1A:
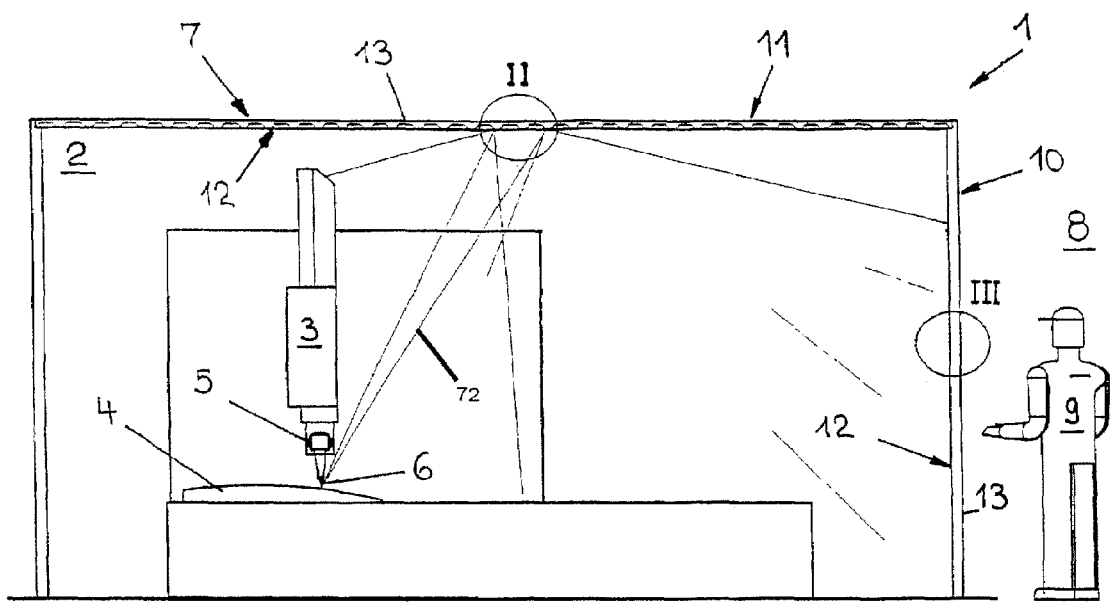
FIG. 1A is a cross-sectional side view of a workroom in the form of a laser safety cabin, having a laser processing device and a workroom partition.
Figure 1B:
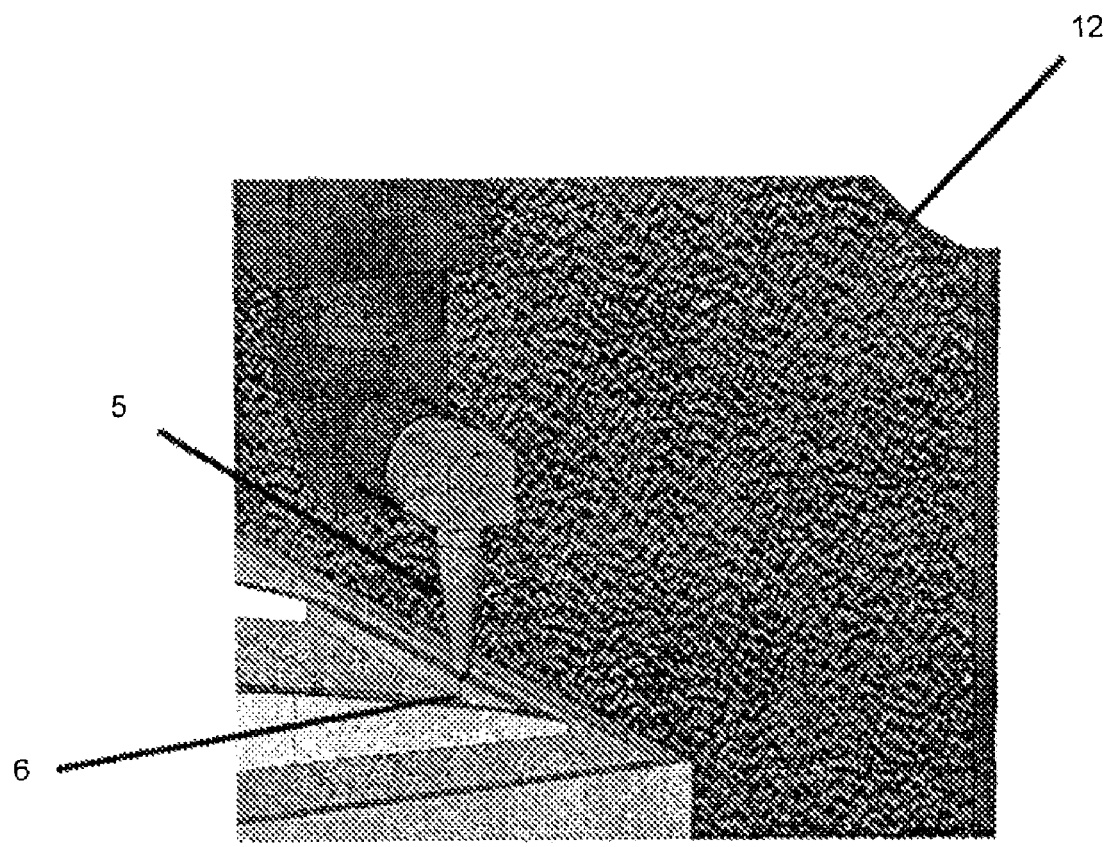
FIG. 1B is a perspective view of the workroom of FIG. 1 showing a laser beam impinging upon a workpiece.
Figure 1C:
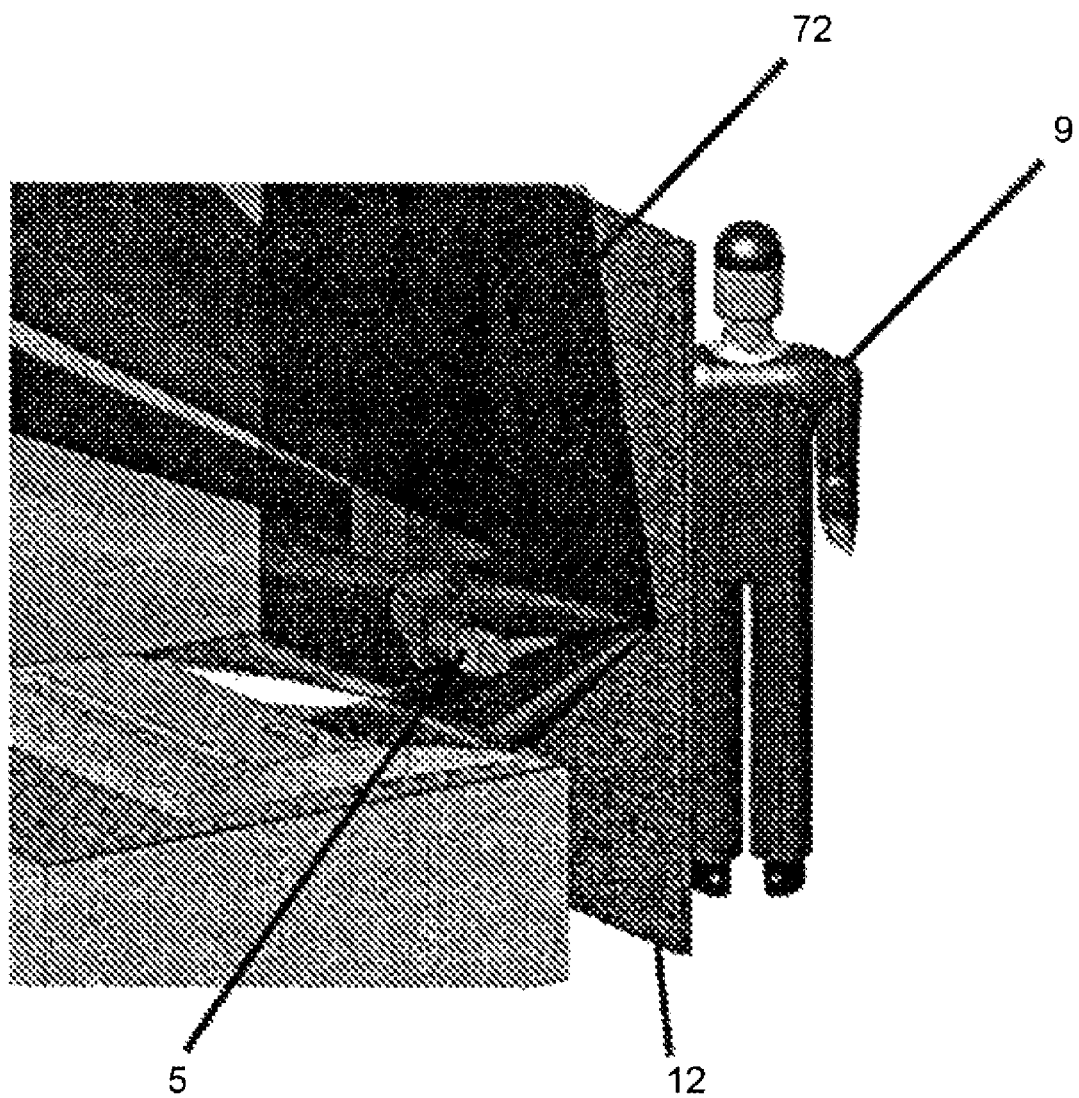
FIG. 1C is a perspective view of the workroom of FIG. 1 showing the laser beam directed to the workroom partition.

Referring to FIGS. 1A-1C, a workroom 1 in the form of a laser safety cabin accommodates in the interior 2 of the workroom a laser processing device 3, which in the example illustrated is in the form of a laser cutting device for the 3D processing of workpieces 4. In normal cutting operation, a laser beam 6 is directed from a laser cutting head 5 of the laser processing device 3 onto the workpiece 4 to be processed.

As indicated in FIG. 1A, the laser beam 6 can be partially reflected at the surface of the workpiece 4 into reflected laser radiation 70. The laser radiation radiated from the surface of the workpiece 4 strikes the inner side of a workroom partition 7. The workroom partition 7 surrounds the laser processing device 3 in the manner of a hood and screens the workroom interior 2 with respect to the workroom surroundings 8. An operator 9 remains in the area 8 surrounding the workroom. Or, as indicated in FIG. 1C, the laser beam 6 from the laser cutting head 5 may be accidentally directed toward the workroom partition 7.

The workroom partition 7 includes a vertical wall region 10 and a horizontal ceiling region 11. Both in the wall region 10 and in the ceiling region 11, the workroom partition 7 has a laser beam reflector 12 on its inner side facing the laser processing unit 3. The laser beam reflector 12 can be formed by the surface of blanks of 1 mm thick aluminum sheet. In the ceiling region 11 of the workroom partition 7, trapezoidal sheeting (sheeting having a trapezoidal cross section) can be provided as the sheeting blanks. Both in the wall region 10 and in the ceiling region 11 of the workroom partition 7 the sheeting blanks are bolted to an outer layer or outer shell 13 of the workroom partition 7. The outer shell 13 of the workroom partition 7 can be made from two-millimeter thick sheet steel.

The laser beam reflector 12 has a material and a design to enable the laser beam reflector 12 to reflect the majority (that is, greater than 50%) of the laser radiation and to therefore prevent the laser radiation from leaving the interior 2 of the workroom 1 or to enter the workroom surroundings 8. Thus, the laser beam reflector 12 should be made of a highly-reflective material such as, for example, aluminum, silver, chrome, molybdenum, chromium, copper, gold, nickel, palladium, platinum, stainless steel, or suitable alloys. The geometry of the laser beam reflector 12 is such that radiation incident on the laser beam reflector 12 is not directionally reflected by the laser beam reflector 12; rather, radiation incident on the laser beam reflector 12 is diffusely reflected by the laser beam reflector 12. To enable such diffuse reflection, the surface of the laser beam reflector 12 should be an uneven or granular surface such that an incident ray is seemingly reflected at a number of angles. For example, as shown in FIG. 1C, laser radiation 72 is diffusely reflected from the laser beam reflector 12.

Figure 2:
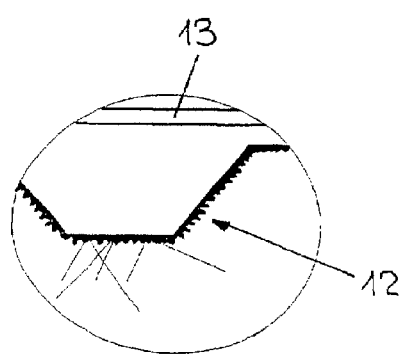
FIG. 2 is a cross-sectional side view of detail II from FIG. 1.
Figure 3:
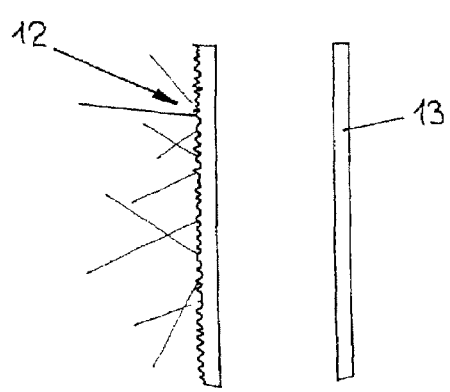
FIG. 3 is a cross-sectional side view of detail III from FIG. 1.

The aluminum sheet of the laser beam reflector 12 is commercially available. In the construction trade it is used, for instance, inter alia, as facade or roof cladding. The sheet surface that forms the laser beam reflector 12 is shiny and has a three-dimensional surface structure, which in FIGS. 2 and 3 is shown in outlines. In FIG. 1C, for the sake of simplicity, the laser beam reflector 12 is shown as a flat surface.

The three-dimensional surface structure of the aluminum sheet used for the laser beam reflector 12 can be irregular and correspond approximately to the surface structure of grained leather, which includes a random pattern of wrinkles made of valleys and crevasses. In the trade, this surface structure can be obtainable under the name "stucco textured".

Alternatively, the aluminum sheet can have a regularly structured surface, for example, having spherical structures.

The reflection characteristics of the sheet surface are important. For one thing, one must ensure that the majority of the laser radiation originating from the laser processing device 3 is reflected at the sheet surface forming the laser beam reflector 12. This precondition is satisfied to a great extent by the shiny aluminum surface of the exemplary embodiment shown forming the laser beam reflector 12. The laser beam reflector 12 thus reflects around 99% of the laser radiation incident upon it. This extremely high reflectance is achieved at the wavelength of the laser light striking the laser beam reflector 12 in the example case shown. The wavelength of the laser light in turn is dependent on the construction of the beam source. A $CO_2$ generator is used to generate the laser beam 6. If the laser light incident on the laser beam reflector 12 were to be generated by means of a NdYAG laser, then a reflectance of around 90% can be achieved with the shiny aluminum surface of the exemplary embodiment. By virtue of the selected surface structure of the laser beam reflector 12, a reflectance of this order of magnitude is achieved even when the laser beam reflector 12 is affected by contamination, which can occur in the immediate vicinity of the laser cutting devices.

By virtue of the high reflection factor of the laser beam reflector 12, under the action of the laser light incident on the laser beam reflector 12, only slight warming of the laser beam reflector 12 and hence of the entire workroom partition 7 occurs. The workroom partition 7 therefore gains a long service life.

At the same time, the surface structure of the laser beam reflector 12 provides for a diffuse reflection of the incident laser light, as indicated in FIGS. 2 and 3. The energy densities in the laser light radiated from the laser beam reflector 12 are therefore at a merely low level. In particular, the energy densities are too low to be able to cause damage in the workroom interior 2, for example, to the laser processing device 3.

Consequently, for example, protective covers otherwise required for bellows of the laser processing device 3 can be dispensed with.

The laser beam reflector 12 displays the described protective effect towards the inside and towards the outside even during irregular operating states of the laser processing device 3, for instance when the laser beam 6 from the laser cutting head 5 is inadvertently directed onto the laser beam reflector 12.

Figure 4:
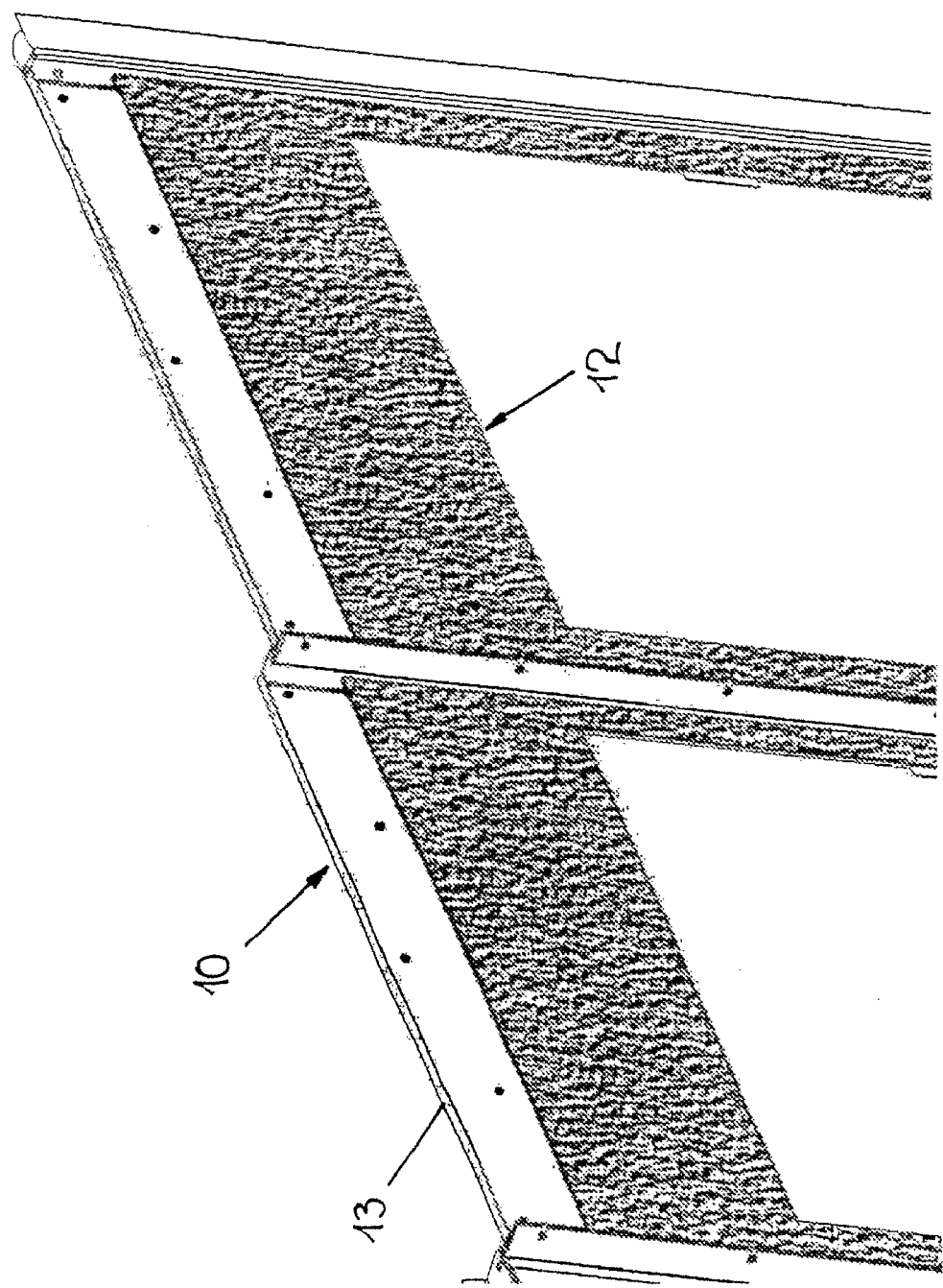
FIG. 4 is a perspective view from an interior of a portion of the workroom partition of FIG. 1.

FIG. 4 shows the laser beam reflector 12 and its relationship to the outer shell 13 of the workroom partition 7 in the view from the interior 2 of the workroom. The region of the partition 7 illustrated is provided with window cut-outs. The surface structure of the laser beam reflector 12 is clearly discernible.

Figure 5:
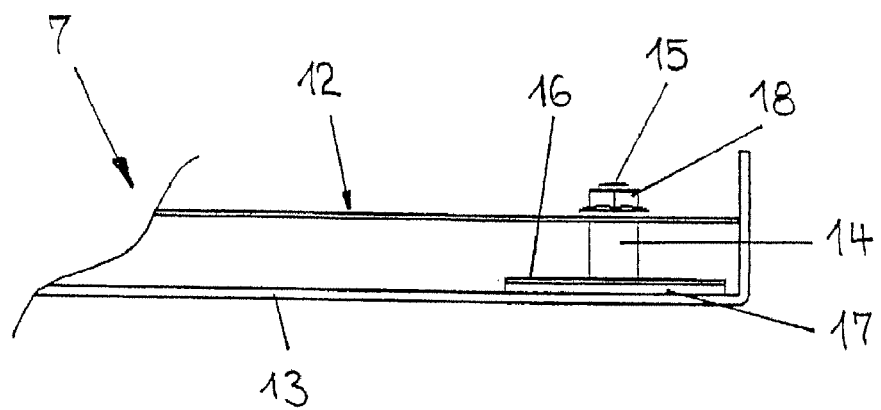
FIG. 5 is a cross-sectional side view of a portion of a workroom partition that can be used for the workroom of FIG. 1.

FIG. 5 shows in detail a bolted connection between the laser beam reflector 12 and the outer shell 13 of the workroom partition 7. According to this design, the laser beam reflector 12 is held spaced by means of a spacer sleeve 14 from the outer shell 13. The resulting gap between the laser beam reflector 12 and the outer shell 13 of the workroom partition 7 provides for thermal insulation of the outer shell 13 with respect to the laser beam reflector 12 exposed to the laser radiation. A screw bolt 15 that is welded to a base plate 16 at its longitudinal end associated with the outer shell 13 passes through the spacer sleeve 14. The base plate 16 is adhesively secured to a pre-cut part 17 of foam rubber that is self-adhesive on both sides. The pre-cut part 17 in turn is adhesively secured on its side remote from the base plate 16 to the outer shell 13. At the free end of the screw bolt 15, the laser beam reflector 12 is braced between a nut 18 and the spacer sleeve 14. Corresponding connections between the laser beam reflector 12 and the outer shell 13 of the workroom partition 7 are made at the remaining fixing points of the laser beam reflector 12.

To dismantle the laser beam reflector 12, either the nuts 18 or the adhesive connections between the pre-cut parts 17 of the individual fixing devices and the outer shell 13 are undone. To re-mount the laser beam reflector 12, in the last-mentioned case the old pre-cut parts 17 at the base plates 16 of the various fixing devices are replaced by new pre-cut parts with as yet unused adhesive surfaces. Subsequently, the laser beam reflector 12 can be adhesively secured with the new pre-cut parts 17 mounted on the base plates 16 to the inner side of the outer shell 13 of the workroom partition 7.

Figure 6:
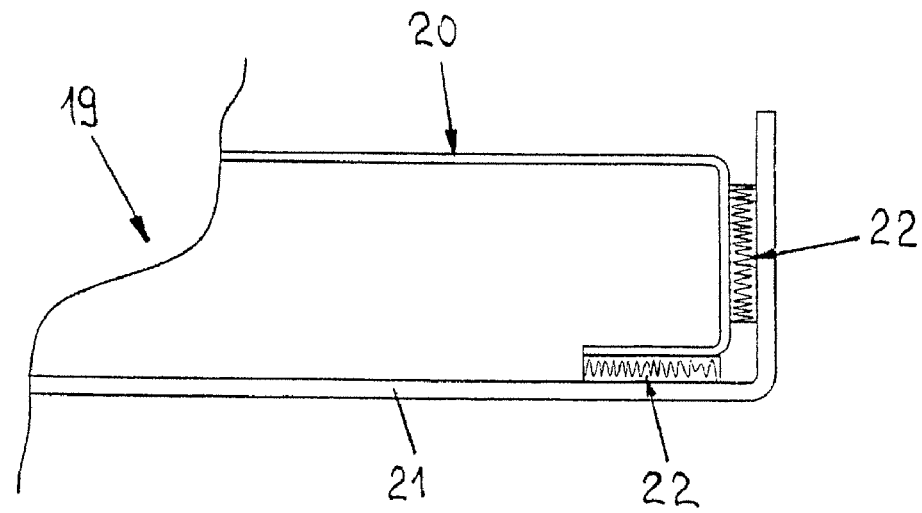
FIG. 6 is a cross-sectional side view of a portion of a workroom partition that can be used for the workroom of FIG. 1.

FIG. 6 shows a workroom partition 19 with a laser beam reflector 20 and an outer layer or outer shell 21. The laser beam reflector 20 is bent at its edge into a U-shape. One or more hook and loop connections 22 are made between two sides of the U-shaped bent configuration of the laser beam reflector 20 and the outer shell 21. For that purpose, portions of customary hook and loop strip are arranged on the one hand on the laser beam reflector 20 and on the other hand on the outer shell 21. The hook and loop connections 22 permit an easy-to-manage mounting and demounting of the laser beam reflector 20.

Both the laser beam reflector 12 according to FIG. 5 and the laser beam reflector 20 according to FIG. 6 are formed by a "stucco textured" surface of blanks of aluminum sheet. For reasons of simplification of the drawings, a detailed portrayal of the surface structure has not been shown in FIGS. 5 and 6.

Figure 7:
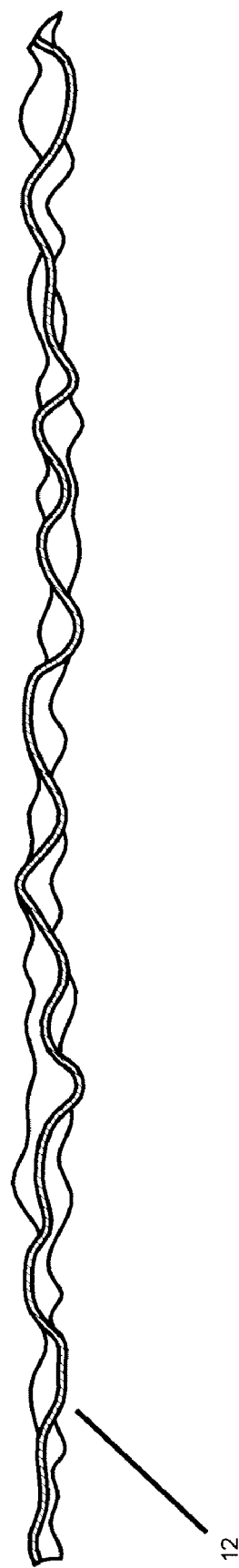
FIG. 7 is a cross-sectional view of a laser beam reflector of the workroom partition of FIGS. 1-6.

Referring to FIG. 7, the laser beam reflector 12 has a cross-sectional geometry of grained leather. Such a reflector 12 can be purchased pre-fabricated, and then attached to the outer shell 13 using any suitable technique, for example, either of the techniques shown in FIGS. 5 and 6. In this way, the laser beam reflector 12 need to be fabricated using a complicated process but can be purchased and applied to the outer shell 13.

Figure 8:
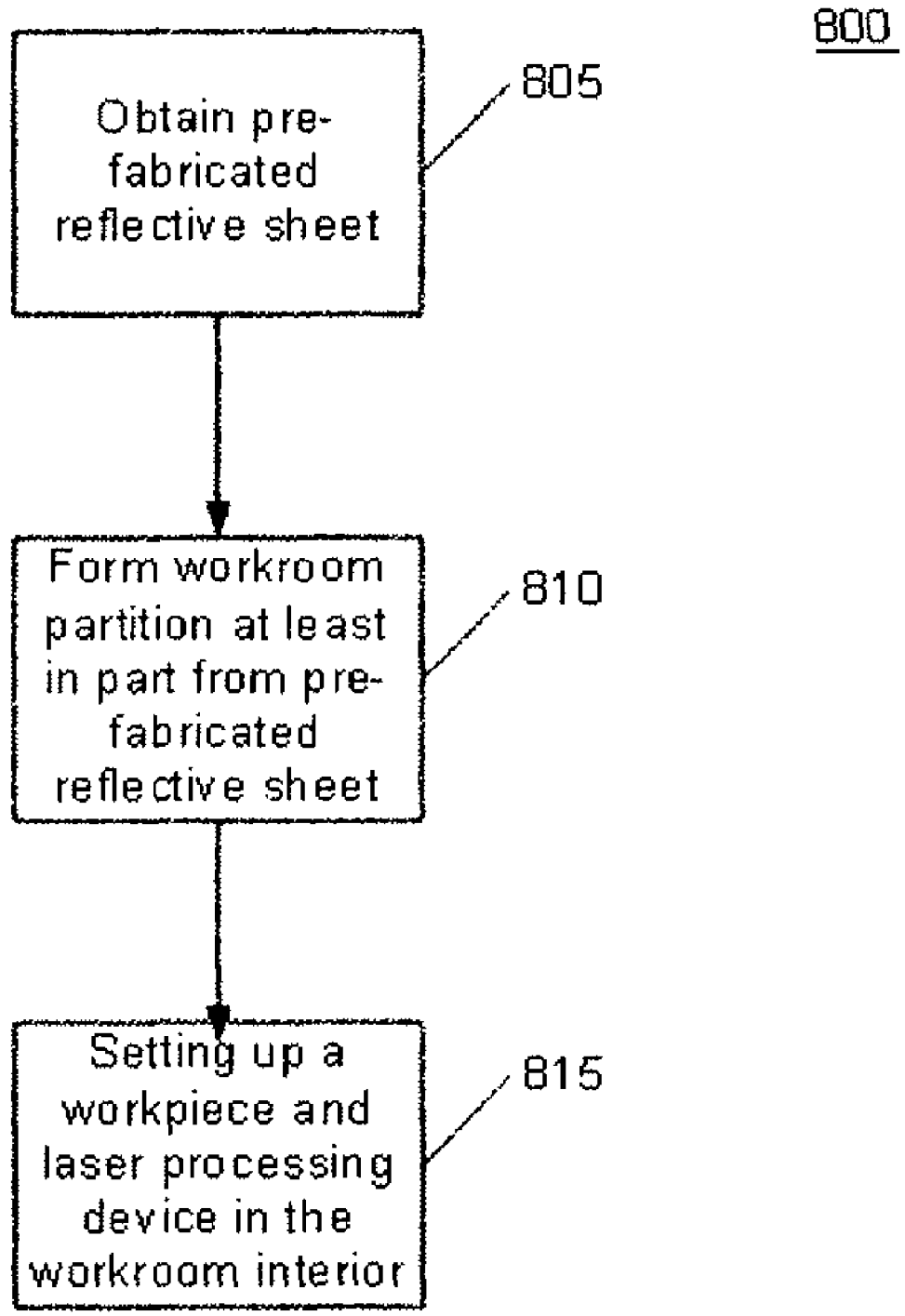
FIG. 8 is a flow chart of a procedure for setting up the workroom.

Referring to FIG. 8, a procedure 800 is performed for forming the workroom 1. Initially, a pre-fabricated reflective sheet of material 12 is obtained from a commercial manufacturer (step 805). The pre-fabricated reflective sheet of material 12 has a grained reflective surface structure, as discussed above. Moreover, the material selected for the sheet can be a material that is selected depending on a wavelength of the laser beam produced by the laser in the workroom 1 such that the majority of the laser radiation is reflected by the laser beam reflector on the grained surface structure. For example, the sheet can be a pre-fabricated sheet of aluminum material.

Next, a workroom partition 7 is formed at least in part from the obtained pre-fabricated reflective sheet (step 810). The workroom partition 7 is formed by, for example, applying the pre-fabricated reflective sheet 12 to an outer shell 13 as discussed above. Moreover, the workroom partition can be configured to enclose the workroom interior such that the grained surface structure of the pre-fabricated sheet faces an interior of a workroom, where the workroom partition 7 separates the workroom interior from the workroom surroundings. The workroom partition 7 can be formed by forming at least four walls and a ceiling to form an enclosed space that will be able to house the laser processing device 3. The workroom partition can be formed by forming at least one window, at least one door, or both a window and a door into at least one of the four walls to enable an operator to view or access the workroom interior.

Next, a workpiece 4 and a laser processing device 3 including a laser are housed or configured in the interior of the workroom 1 such that a laser beam from the laser is at least partly directed to the workpiece for processing of the workpiece (step 815). A majority of any laser radiation that might be incident on the grained surface structure of the workroom partition 7 is diffusely reflecting such that laser radiation is mostly contained within the workroom interior without causing damage to the workroom interior. Laser radiation can be incident on the grained surface structure due to reflections off of other devices in the workroom interior or due to a repositioning of the laser processing device 3.

The workroom partition can be formed by disconnectably connecting the pre-fabricated reflective sheet to an outer layer of the workroom partition, where the outer layer is arranged to face the workroom surroundings and to be remote from the laser processing device. The workroom partition can be formed by forming a gap between the pre-fabricated reflective sheet and an outer layer of the workroom partition, where the outer layer is arranged to face the workroom surroundings and to be remote from the laser processing device.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A workroom partition between a workroom interior of a workroom and a workroom surroundings, where the workroom is provided with a laser processing device, the workroom partition comprising:

on its inner side facing the laser processing device, a laser beam reflector formed from pre-fabricated reflective sheet of aluminum material having a diffusely reflective aluminum surface with a reflective surface structure that corresponds to the surface structure of grained leather, the reflective surface structure facing the laser processing device and diffusely reflecting the majority of laser radiation incident on the laser beam reflector and originating from the laser processing device.

2. The workroom partition of claim 1, wherein the laser beam reflector is matched in terms of its material to the wavelength of the laser radiation to be reflected.

3. The workroom partition of claim 1, wherein the grained reflective surface structure includes a shiny metal surface.

4. The workroom partition of claim 1, wherein the laser beam reflector comprises at least partially a reinforcing deformation.

5. The workroom partition of claim 1, wherein the laser beam reflector includes a portion that is at least partially in the form of trapezoidal metal sheeting.

6. The workroom partition of claim 1, further comprising an outer layer that faces the workroom surroundings and is remote from the laser processing device, wherein the laser beam reflector is disconnectably connected to the outer layer of the workroom partition.

7. The workroom partition of claim 6, wherein the laser beam reflector is connected to the outer layer of the workroom partition such that a gap is formed between the laser beam reflector and the outer layer of the workroom partition.

8. A workroom comprising:
a laser processing device; and
a workroom partition that separates a workroom interior from a workroom surroundings and houses the laser processing device, wherein the workroom partition comprises:
on its inner side facing the laser processing device, a laser beam reflector formed from pre-fabricated reflective sheet of aluminum material having a diffusely reflective aluminum surface with a reflective surface structure that corresponds to the surface structure of grained leather, the reflective surface structure facing the laser processing device and diffusely reflecting the majority of laser radiation incident on the laser beam reflector and originating from the laser processing device.

9. The workroom of claim 8, wherein the laser beam reflector is matched in terms of its material to the wavelength of the laser radiation to be reflected.

10. The workroom of claim 8, wherein the grained reflective surface structure includes a shiny metal surface.

11. The workroom of claim 8, wherein the laser beam reflector comprises at least partially a reinforcing deformation.

12. The workroom of claim 8, wherein the laser beam reflector includes a portion that is at least partially in the form of trapezoidal metal sheeting.

13. The workroom of claim 8, wherein the workroom partition comprises an outer layer that faces the workroom surroundings and is remote from the laser processing device, wherein the laser beam reflector is disconnectably connected to the outer layer of the workroom partition.

14. The workroom of claim 13, wherein the laser beam reflector is connected to the outer layer of the workroom partition such that a gap is formed between the laser beam reflector and the outer layer of the workroom partition.

15. A method comprising:
obtaining a pre-fabricated reflective sheet of aluminum material having a diffusely reflective aluminum surface with a reflective surface structure that corresponds to the surface structure of grained leather;
forming a workroom partition at least in part from the obtained pre-fabricated reflective sheet such that the grained surface structure faces an interior of a workroom, where the workroom partition separates the workroom interior from the workroom surroundings;
housing a workpiece and a laser processing device including a laser in the interior of the workroom such that a laser beam from the laser is at least partly directed to the workpiece for processing of the workpiece; and
diffusely reflecting a majority of laser radiation incident on the grained surface structure such that laser radiation is mostly contained within the workroom interior without causing damage to the workroom interior.

16. The method of claim 15, further comprising selecting a material of the laser beam reflector depending on a wavelength of the laser beam produced by the laser in the workroom such that the majority of the laser radiation is reflected by the laser beam reflector on the grained surface structure.

17. The method of claim 15, wherein forming the workroom partition includes disconnectably connecting the pre-fabricated reflective sheet to an outer layer of the workroom partition, where the outer layer is arranged to face the workroom surroundings and to be remote from the laser processing device.

18. The method of claim 15, wherein forming the workroom partition includes forming a gap between the pre-fabricated reflective sheet and an outer layer of the workroom partition, where the outer layer is arranged to face the workroom surroundings and to be remote from the laser processing device.

19. The method of claim 15, wherein forming the workroom partition at least in part from the obtained pre-fabricated reflective sheet includes applying the pre-fabricated reflective sheet to a ceiling of the workroom partition.

20. The method of claim 15, wherein forming the workroom partition includes enclosing the workroom interior with the workroom partition.

21. The method of claim 15, wherein forming the workroom partition includes forming at least four walls and a ceiling to form an enclosed space.

22. The method of claim 15, wherein forming the workroom partition includes forming at least one window, at least one door, or both a window and a door into at least one of the four walls to enable an operator to view the workroom interior.

* * * * *